(12) United States Patent
Prinz

(10) Patent No.: US 10,435,253 B2
(45) Date of Patent: Oct. 8, 2019

(54) METHOD OF IN-LINE TESTING DEVICES AND TESTING APPARATUS

(71) Applicant: Wilco AG, Wohlen (CH)

(72) Inventor: Heino Prinz, Buttikon (CH)

(73) Assignee: WILCO AG, Wohlen (CH)

( * ) Notice: Subject to any disclaimer, the term of this patent is extended or adjusted under 35 U.S.C. 154(b) by 111 days.

(21) Appl. No.: 14/905,851

(22) PCT Filed: Jul. 19, 2013

(86) PCT No.: PCT/EP2013/065317
§ 371 (c)(1),
(2) Date: Jan. 18, 2016

(87) PCT Pub. No.: WO2015/007342
PCT Pub. Date: Jan. 22, 2015

(65) Prior Publication Data
US 2016/0167899 A1    Jun. 16, 2016

(51) Int. Cl.
*B65G 54/02* (2006.01)
*G01N 35/04* (2006.01)
*G01N 35/02* (2006.01)
*G01N 21/84* (2006.01)
*B07C 5/36* (2006.01)

(52) U.S. Cl.
CPC ............. *B65G 54/02* (2013.01); *G01N 35/02* (2013.01); *G01N 35/04* (2013.01); *B07C 5/36* (2013.01); *G01N 2021/845* (2013.01)

(58) Field of Classification Search
CPC ...................................................... B07C 5/36
See application file for complete search history.

(56) References Cited

U.S. PATENT DOCUMENTS

| | | | | |
|---|---|---|---|---|
| 3,598,907 A | * | 8/1971 | Drinkuth | G01B 11/022 348/127 |
| 3,627,423 A | * | 12/1971 | Knapp | G01N 21/53 250/573 |
| 3,651,937 A | * | 3/1972 | Kronseder | B07C 5/126 209/524 |
| 3,746,165 A | * | 7/1973 | Ford | G01N 21/9009 209/524 |
| 3,749,025 A | * | 7/1973 | Giraud | B65G 23/00 104/25 |

(Continued)

FOREIGN PATENT DOCUMENTS

| | | |
|---|---|---|
| EP | 0 160 523 B1 | 1/1989 |
| EP | 0 400 663 B1 | 8/1990 |
| EP | 0 721 872 B1 | 7/1996 |

OTHER PUBLICATIONS

G. Coquery and J. Sebillaud, "Airport baggage handling system using u asynchronous linear motors," in The 18th International Conference on Magnetically Levitated Systems and Linear Drives, vol. 2, 2004, pp. 864-871.*

(Continued)

*Primary Examiner* — Harshad R Patel
(74) *Attorney, Agent, or Firm* — Pearne & Gordon LLP

(57) ABSTRACT

Devices to be tested are conveyed towards, into and from a testing station and are tested there being kept stationary. Conveying into and from the testing station is performed by a mover of a linear motor, which is controllably operated in a stepped manner.

21 Claims, 2 Drawing Sheets

(56) References Cited

U.S. PATENT DOCUMENTS

Figure 1:
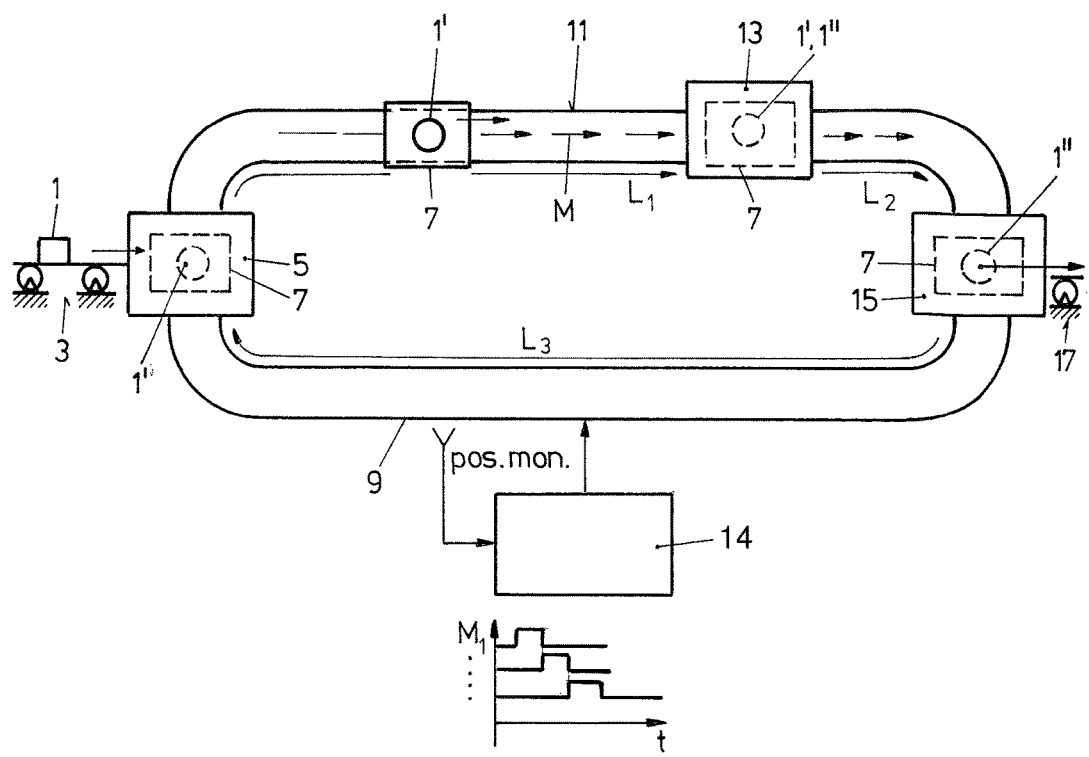

| | | | | |
|---|---|---|---|---|
| 4,136,930 | A * | 1/1979 | Gomm | G01N 21/8851 250/223 B |
| 4,915,237 | A * | 4/1990 | Chang | B07C 5/122 198/406 |
| 4,922,830 | A * | 5/1990 | Fujita | B65G 54/02 104/290 |
| 4,997,552 | A | 3/1991 | Schlinkmann | |
| 6,012,344 | A * | 1/2000 | Halbo | B08B 9/46 198/339.1 |
| 6,275,603 | B1 * | 8/2001 | Cronshaw | G01N 21/9027 250/223 B |
| 7,560,720 | B2 * | 7/2009 | Voigt | G01N 21/9027 209/524 |
| 8,405,826 | B2 * | 3/2013 | Till | B07C 5/3408 356/237.1 |
| 2003/0089581 | A1 * | 5/2003 | Thompson | B65G 23/18 198/619 |
| 2004/0261363 | A1 * | 12/2004 | Deckert | B65C 3/065 53/415 |
| 2006/0011093 | A1 * | 1/2006 | Jensen | B60L 13/04 104/282 |
| 2006/0117708 | A1 * | 6/2006 | Thielmann | B65C 9/045 53/281 |
| 2012/0049063 | A1 * | 3/2012 | Hatakeyama | G01N 23/225 250/307 |
| 2013/0037384 | A1 * | 2/2013 | Reinisch | G01D 5/245 198/464.2 |
| 2016/0251169 | A1 * | 9/2016 | Stefanko | B65G 47/261 |
| 2016/0281789 | A1 * | 9/2016 | Kleinikkink | B65G 45/02 |

OTHER PUBLICATIONS

Langnau, Leslie, "Lessons from an engineering fiasco," Aug. 2000, 6pp. Accessed online Dec. 26, 2017 <http://www.machinedesign.com/linear-motion/lessons-engineering-fiasco>.*

International Search Report for PCT/EP2013/065317 dated Jul. 24, 2014.

Written Opinion for PCT/EP2013/065317 dated Jul. 24, 2014.

* cited by examiner

METHOD OF IN-LINE TESTING DEVICES AND TESTING APPARATUS

The present invention is directed on a method of in-line testing devices and on a testing apparatus.

In spite of the fact that the present invention was recognized by the inventor in context with visual inspection of transparent containers, especially of transparent containers containing a liquid and to be tested whether or not such liquid in the containers contains solid material particles, the findings leading to the present invention may be applied to a multitude of in-line testing methods for devices as will become apparent to the skilled artisan reading the present application.

Consequently, the present invention will first be addressed under a more generic aspect.

Customary in-line conveying of devices is performed with heavy conveyer systems as by star-wheel conveyers.

If testing of the devices in-line conveyed requires a complete stand still of the devices to be tested with respect to a testing station, the conveyer is operated in a stop and go stepwise mode, if the devices remain on the conveyor during the testing step. The forces to accelerate and decelerate the large inertias of the conveyer including all the devices in-line transported thereon, must be high.

The higher that the throughput rate of such in-line testing shall be, the more frequent become the conveying steps, resulting in increasingly high dynamic forces to act upon the respective drives, gears and bearings of the conveyer.

Additionally high pulse electric energy is to be applied. Moreover, the duration of the testing step may easily govern the overall throughput rate as it is possibly the longest step in the chain of processing steps along the conveying path of the devices.

It is an object of the present invention to improve in-line testing methods as exemplified above and to provide a respectively improved testing apparatus.

This is realized by the method of in-line testing devices, which comprises in-line conveying devices towards, into and from a testing station. A testing step is performed on selected one of said in-line conveyed devices in and by the testing station. Thereby, the addressed selected devices are kept stationer in the testing station with respect to a translatory movement relative to the addressed testing station.

This means that within the testing station a device to be tested there, does not move relative to the testing station along either one of the three spacial directions. This stationarity with respect to translatory movement does nevertheless not exclude that the respective device in the testing station might be rotated about a central axis of the addressed device, because by such a rotation, no translatory movement is established between the device and the testing station.

The addressed method according to the present invention, further comprises conveying the selected device into and from the testing station and holing the device in said testing station during the testing step on a mover of a linear motor which is controllably movement-operated in a stepped manner.

Linear motors are widely known in the art. A linear motor is a drive arrangement with a stator and with a mover. For electric rotary motors the "mover" would be called a "rotor". The mover is moved along the stator of a linear motor by so called "travelling electromagnetic waves" as perfectly known to the skilled artisan. Such travelling electromagnetic waves are generated along the stator by time controlled excitation of electromagnets disposed all along the stator of the linear motor. The stator and thus the trajectory path for the mover travelling along the stator may practically be of any desired shape. An electric linear motor exhibits very high accelerations as well as very high travelling speeds. The mover may be conceived light-weight so that the electromagnetic dynamic forces to be generated and interacting between the stator and the mover may be rather small. This also due to highly efficient magnetic coupling between the stator and the mover.

By exploiting the addressed characteristics of an electric linear motor to convey the addressed selected devices into and from the testing station and for holding said devices in the testing station, with respect to translatory movement stationer, the selected devices may be controlled for high acceleration and high speed movement, thereby favorising step-vise high throughput rates. Moreover and as will be addressed later on, conveying the addressed selected devices by means of a electric linear motor makes it possible, to tailor the overall throughput rate for tested devices, largely independent from the time duration of a testing step in the testing station.

In one embodiment of the method, according to the invention, which may be combined with any embodiment as will be subsequently addressed unless in contradiction, the stator of the linear motor is provided as a closed loop.

Thereby, the one or more than one mover riding on the stator of the electric linear motor may be flowing along the stator in a stepped manner and principally in a one directional flow.

In a good embodiment of the method according to the present invention, which may be combined with any of the pre-addressed and with all embodiments subsequently addressed, if not contradiction therewith, at least two of the addressed movers are provided on the linear motor, simultaneously carrying each one or more than one of the addressed selected devices. Please note that if we speak of "a device" throughout the present description and claims, we also understand under this term a batch of more than one device. The more than one move are individually movement-controlled.

By this embodiment the throughput rate of selected devices, having been tested, is raised. This is especially true, if the addressed embodiment is further tailored to have more than one of the addressed testing station.

This allows the overall method to become substantially independent from the time duration, which is necessitated for testing a device or a batch of devices in the testing stations as provided, which preferably perform testing during substantially equal testing time spans.

In a further embodiment of the method in which at least two of the movers are provided along the stator of the linear motor, the position of each of the movers along the stator of the linear motor is monitored.

This may be performed by a multitude of different techniques e.g. electro optically by sensing individually movers, or may be performed just by monitoring the moving path of each of the movers, as by monitoring electromagnetic coupling of each mover with respect to the stator.

Monitoring the position of each of the movers provides information for individually controlling the operation of the addressed movers to avoid collision.

In one embodiment of the method according to the invention, which may be combined with any of the pre-addressed embodiments and with any of the embodiments still to be addressed, if not in contradiction, by the testing station, electromagnetic radiation is sensed from the addressed selected device in such station. Thereby, generically, sensing such radiation from the device becomes most accurate if during the sensing time span the device is held stationer with respect to translatory movement and relative to a sensing device of the testing station.

In an embodiment of the just addressed embodiment, the device is a liquid filled container. A wall of the container and the addressed liquid are transparent to the addressed radiation. Sensing comprises single or multiple subsequent standstill picturing, which picturing is sensitive to the addressed radiation. Thus, if the wall of the container and the liquid are transparent to light in the visible spectrum range, the addressed sensing by picturing, may be realize by a photo camera tailored for single or multiple subsequent picturing. Single or multiple picturing is thereby performed as the device performs no translatory movement with respect to such camera.

In an embodiment of the just addressed embodiment, the method according to the invention comprises spinning the liquid in the container being stationary non-spinning. The container thereby resides on the mover and spinning is performed about a central axis of the container during the addressed sensing. This may be performed by subjecting the container with the liquid contained therein to a spinning rotation before arriving to the testing station, which may be performed by a rotary or spinning drive on the mover or by a rotary or spinning drive remote from the mover e.g. in a spinning station upstream the testing station. By the fact that the container in the testing station is preferably completely stationer also with respect to rotational movement or spinning and the liquid therein continues spinning about the addressed axis, multiple picturing of the stationer container and of the rotating liquid allows to detect solid material particle in the liquid.

In an embodiment of the just addressed embodiment, picturing is performed with a picturing device of the testing station which has a picturing axis obliquely intersecting the addressed central axis about which the liquid is spinning as well as a plane containing a bottom surface of the container. Thus, in fact the optical axis of the picturing device intersects the rotary axis of the liquid in one point, and the addressed plane in which the bottom surface of the container resides on the mover, in a second point. This allows to detect also solid particles in the liquid, which e.g. due to their weight, are not travelling freely in the spinning liquid.

Thus, in one embodiment of the method according to the invention, the testing station performs multiple subsequent picturing, preferably in the visible spectrum of light and the result of such picturing is exploited as an indication of solid particles present in the liquid contained in the container.

In a further embodiment of the method according to the invention, which may be combined with any of the pre-addressed embodiments, all devices in-line conveyed are selected to be subjected to testing in the one or more than one testing stations provided along the electric linear motor.

The present invention further proposes an in-line device-testing apparatus, which comprises at least one testing station. The testing apparatus further comprises a conveyer constructed to convey at least one of said devices towards, into and from the testing station and for holding the selected device or, in batch operation, selected devices in the testing station during testing. The conveyor is a linear motor with at least one mover constructed to hold the selected device or, for batch operation, the more than one selected devices.

In an embodiment of the addressed apparatus, which may be combined with any of the subsequently addressed embodiments, unless in contradiction, the stator of the linear motor is shaped in a closed loop.

In one embodiment of the apparatus according to the invention, which may be combined with any of the pre-addressed embodiments and with all embodiments of the apparatus still to be addressed, unless in contradiction, two of the addressed movers are provided and a control unit adapted to individually control movement-operation of the at least two movers along the stator of the linear motor is provided.

In a further embodiment of the just addressed embodiment, the apparatus comprises more than one of the addressed testing stations along the linear motor.

Still in a further embodiment of the apparatus according to the invention, the apparatus comprises sensing mean for the position of the addressed mover or movers along the trajectory path along of the electric linear motor.

In a further embodiment of the apparatus, which may be combined with any of the pre-addressed embodiments and with any embodiment still to be addressed, unless in contradiction, the testing station or the testing stations comprise a radiation sensing arrangement.

In a further embodiment of the apparatus according to the invention, which may be combined with any of the pre-addressed embodiments and with any embodiment of the apparatus still to be addressed, unless in contradiction, the at least one mover is adapted to hold a container with a liquid content, as a device, whereby the testing station comprises a standstill picturing arrangement for picturing the container and the liquid contained therein, once or more than once subsequently.

In a further embodiment of the just addressed embodiment, the apparatus according to the invention comprises a spinning drive for the container as residing on the mover and about a central axis of a container on the addressed mover. The spinning drive may thereby be provided upstream the standstill picturing arrangement and is preferably constructed to first exhibit on the container and the liquid contained therein spinning operation, then to stop spinning operation upon the container, leaving the liquid therein, due to its inertia, ongoing by spinning. Such spinning is being maintained during the addressed picturing.

In a further embodiment of the apparatus according to the invention, the addressed picturing arrangement comprises a camera and the mover is adapted to hold the container bottom down. With the bottom of the container defining a plane perpendicular to the central axis, about which first the container and the liquid then only the liquid is spinning, a picturing axis of the camera intersects the central axis as well as the plane, on which the bottom surface of the container is positioned on the mover.

In a further embodiment of the apparatus according to the invention, the apparatus comprises an evaluation unit, an input of which being operationally connected to a picture output of the camera. The evaluation unit generates, at an output thereof, a signal which is indicative of whether a container having been tested in the testing station has solid particles in its liquid content.

The invention further is directed on a method of manufacturing tested devices, which comprises manufacturing untested devices and then subjecting such untested devices to a testing method as was addressed above and according to the addressed embodiments of such method.

The invention shall now be further exemplified with the help of figures:

The figures show:

FIG. 1; in a top view representation, simplified and schematically a first embodiment of an apparatus according to the present invention and operating the methods according to the invention.

Figure 2:
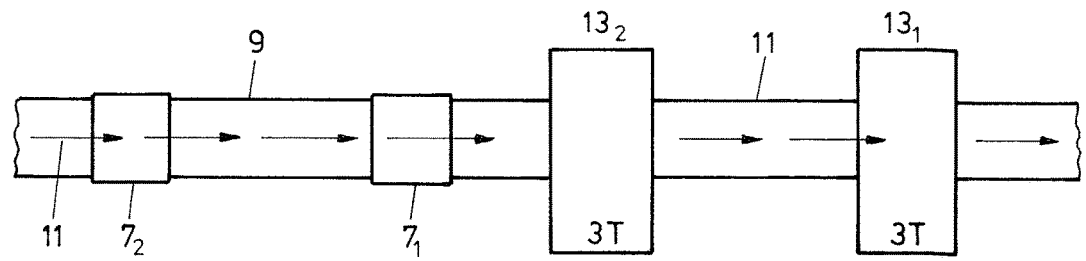

FIG. 2; simplified and schematically, a part of a linear motor as applied in the embodiment of FIG. 1 and in a different realization form.

Figure 3:
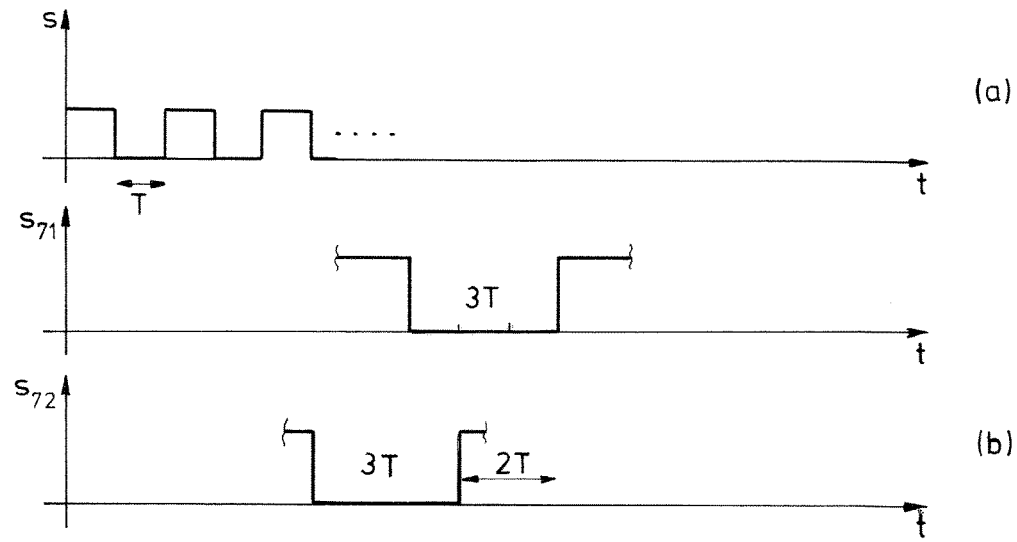

FIG. 3 a simplified timing diagram resulting from an embodiment of the apparatus and methods according to FIG. 2.

Figure 4:
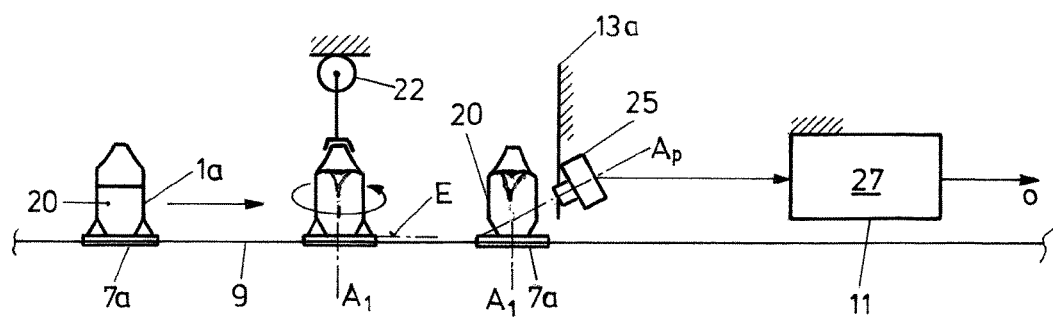

FIG. 4 in a still further simplified representation, a specific embodiment of the apparatus and methods according to the present invention, for testing liquid filled containers upon presence/non-presence of solid material particles in the liquid.

FIG. 1 shows, most simplified and schematically, a first embodiment of an apparatus according to the present invention operating the methods according to the invention. Untested devices 1 are in-line conveyed by an input conveyor 3 e.g. a star-wheel conveyor, to a loading station 5. In the loading station 5, a selected one 1' of the in-line arriving devices 1 is loaded on a mover 7 of an electric linear motor 9. As known to the skilled artisan, an electric linear motor 9 comprises a stator 11, which, in a good embodiment of the present invention forms, as shown in FIG. 1, a closed loop. As known within the stator 11, a multitude of subsequent, controllably enabable magnet arrangement is provided as indicated by the subsequent arrows M in FIG. 1.

Each of the controllably, enabable magnet arrangements M may be enabled via a control unit 14. As schematically shown in FIG. 1 and over the time axis t, the magnet arrangements M provided one after the other and along stator 11, are pulse-energized in a subsequent pattern so that a mover 7, which e.g. comprises a part of magnetizable material, as e.g. of ferromagnetic material, is propelled in direction of subsequently energized magnet arrangements M.

After a selected device 1' having been loaded in the loading station 5 on a mover 7 of the electric linear motor 9 and (not shown) being held thereon, the addressed mover 7 is highspeed conveyed along the stator 11 of the electric linear motor 9 into a testing station 13. This is shown in FIG. 1 by the arrow $L_1$. In testing station 13 the mover 7 is brought to complete standstill for the time span necessitated to perform a testing step or testing operation within the testing unit 13. Thereafter the mover 7, still with the device 1' thereon, know having been tested 1", is conveyed —$L_2$— to an unloading station 15, where the tested device 1 is transferred to an output conveyor 17, e.g. again, a star-wheel conveyor. The mover 7 now freed from the device 1" is back-transferred to the loading station 5 according to arrow $L_3$ of FIG. 1, where the addressed mover 7 is re-loaded with the next selected device 1'.

When we speak of "selected devices", which are loaded to the mover 7 of the electric linear motor 9 and are thus tested in testing station 13, such selected devices may be randomly selected out of the in-line stream of devices 1 to be tested or may be selected out of the inline stream of devices 1 at a regular rate, e.g. every $5^{th}$ device or, and in a good embodiment, which will be addressed also later, every device in-line conveyed on input conveyer 3, is tested. It goes without saying that if not all in-line conveyed devices have to be tested those devices 1, which are not to be tested, do bypass the overall arrangement of linear motor 9 and testing station 13, directly to the output conveyor 17, where they are joint by those devices 1", which have been tested and which have positively passed the test.

Nevertheless, it is clearly apparent from FIG. 1 that the electric linear motor 9 may comprise more than one of the movers 7 and that more than one of the addressed mover 7 may carry a device 1' simultaneously. Thus, e.g., a first mover 7 may reside with its respective device 1' in the testing station 13, whereas a second mover 7 is present at the loading station 5 and is there loaded with a device 1 to be tested, whereas, even further, a third mover 7 may be already present in the un-loading station 15 where this third mover 7 is un-loaded from a device 1" having been tested.

Thereby, the throughput rate of tested devices 1" is increased with respect to that embodiment, in which only one mover is provided on the electric linear motor 9.

At this point it should be noted that the electric linear motor 9 with control unit 14 allows most flexibly to provide first e.g. only one mover 7, e.g. for testing operation and then to build up a more complex system by adding more movers to the electric linear motor.

Each of the movers 7 provided at the one electric linear motor 9, is individually movement controlled by the control unit 14.

FIG. 2 shows in a most simplified and schematic representation according to that of FIG. 1, a branch of the looping electric linear motor 9, wherealong two testing stations $13_1$ and $13_2$ are provided, each necessitating the preferably same testing time 3 T for testing.

Further, the linear motor 9 comprises two movers $7_1$ and $7_2$, which are each individually movement-controlled by means of control unit 14 as of FIG. 1.

The advantage of multiple movers and multiple testing stations shall be explained with a simple timing diagram of FIG. 3.

FIG. 3a exemplifies a speed (s) diagram of input conveyor 3 and of output conveyor 17 of FIG. 1, defining for standstill periods with extend T. The throughput rate resulting from conveyor 3 and 17 is the maximum throughput rate of the overall system including the linear motor/testing station system as of FIG. 1 or 2. The maximum rate is thus according to FIG. 3 one device per period 2 T. Assuming now that each of the testing stations $13_1$ and $13_2$ necessitates an integer testing time, which is approximately a multiple of T as e.g. 3 T as shown in FIG. 2, this would in a single testing station approach result in an overall throughput of one device per 3 T.

In FIG. 3(b) $S_{71}$ shows the testing duration of 3 T, during which mover $7_1$ stays stationer in testing station $13_1$ of the system of FIG. 2.

$S_{72}$ represent the time span of 3 T, during which the mover $7_2$ as of FIG. 2 remains stationer in the testing station $13_2$. Loading the two movers $7_1$ and $7_2$ occurs at maximum rate of one device per 2 T. Thus and as may be seen from FIG. 3(b), the two testing stations $13_1$ and $13_2$ of FIG. 2 are loaded with a time lag of 2 T. There results that after the respective testing times of 3 T, the devices, now tested, are output from testing station $3_1$ first, then from testing station $13_2$ with a time lag of 2 T. There results that the output rate, that is the rate with which tested devices, are loaded to the output conveyor 17 as of FIG. 1, is one device per 2 T, which accords with a maximum rate defined by input and output conveyors 3 and 17. Thus, by providing multiple testing stations and multiple movers, it becomes possible to make overall throughput rate of the system or uninfluenced by the amount of time necessitated by the testing stations to perform the testing steps.

So as to properly control movement operation of the movers 7, it might be highly advantageous to monitor their momentary position along the stator 11. This may e.g. be performed by opto-electrically tracking each of the movers along the stator 11 or by monitoring the electromagnetic coupling at each of the magnet arrangements M of the stator 11 and e.g. counting the number of magnetic arrangements, which have successfully been coupled to a mover.

Monitoring the position of the movers along the stator 11, may especially be important for avoiding collision of the movers and to establish proper movement control, if different from the embodiment as shown in FIG. 3, testing time spans are not integral multiples of the standstill time spans of the input and output conveyors and thus an ongoing optimal movement control of the movers 7 is to be practiced by control unit 14.

In FIG. 4 there is shown most schematically and simplified, a further embodiment of the apparatus and methods according to the invention, tailored for special purpose.

On the one or more than one movers 7a of the linear motor 9, shown most schematically in FIG. 4, there is deposited and held, as a device $1_a$ to be tested, a container which is filled with a liquid 20 and which is, in a good embodiment, closed. The liquid 20 as well as the wall of container $1_a$, are transparent to electromagnetic radiation, in the embodiment of FIG. 4 e.g. to light in the visible and/or in the infrared spectrum.

When conveyed along the trajectory path of linear motor 9, the containers 1a are subjected to spinning about a central axis $A_1$ of the container 1a, perpendicular to a plane E which contains the bottom surface of the container resting on mover 7a. Spinning of the container 1a with the liquid contained therein, may be performed by bringing the mover 7a to complete standstill in a spinning station and coupling, as schematically shown in FIG. 4, a spinning drive 22, external and remote from mover 7a, centrally to container 1a. Alternatively such spinning may also be performed by a spinning drive (not shown) which resides on the mover 7a, if the inertia of the mover with container and spinning drive becomes not too large and if electric powering of a spinning drive on the moveable movers 7a may e.g. be realized by batteries or rechargeable batteries on the respective movers.

Irrespective from how spinning is performed, after the container 1a and the liquid therein has been spin-rotated, the spinning drive is disabled from acting upon the container 1a and the container 1a comes to complete standstill. The liquid 20 therein continues nevertheless to rotate in the container for some time. As shown in FIG. 4, it is during this time in which the liquid in the container 1a continues spinning and the container 1a itself is in complete standstill that the container is present in the testing station, schematically shown in FIG. 4 at 13a.

The testing station 13a comprises a picturing device 25 as of a digital fotocamera sensitive in the visible light spectrum or in the infrared light spectrum and/or adapted to make single and especially multiple shot picturing. A respective radiation source as of a light-source (not shown) may be provided for transmitting radiation through the container 1a and the liquid 20 to the device 25.

When the mover 7a is in complete standstill and thus also the container 1a, the picturing device 25 makes preferably multiple picture shots, thus upon the liquid 20, which is still spinning in the container. The output of the picturing device 25 is fed to the input of an evaluating unit 27, which outputs a signal o, which is representative of whether solid material particles are present in the liquid 20 and are thus moving with such liquid, or not. $A_p$ shown in FIG. 4, the picturing axis or optical axis $A_p$ of the picturing device 25 is directed so as to intersect the central axis $A_1$ approximately in a point and the plane E in a second point, thus being inclined towards the bottom surface of the container 1a. By doing so and by multiple picturing it becomes possible to even detect solid material particles in the liquid and on the bottom surface of the container.

As a linear motor, which is perfectly suited to realize the present invention under all its aspect, attention is drawn to the XTS Linear Transport System of Beckhoff Automation GmbH, 33415 Verl, Germany.

Other linear motors may also be suited for realizing the present invention.

What is claimed is:

1. Method of in-line testing devices comprising:
   in-line conveying devices towards, into and from a testing station on a mover of a linear motor that is controllably operated in a stepped manner,
   performing, on a selected one of said in-line conveyed devices, a testing step in and by said testing station, thereby
   keeping said selected device in said testing station stationary with respect to a translatory movement relative to said testing station by holding said device in said testing station during said testing step on the mover of the linear motor,
   sensing an electromagnetic radiation from said device by said testing station wherein said device is a liquid filled container, a wall of the container and the liquid being transparent to said radiation, comprising performing said sensing by said testing station by single or multiple subsequent stand still picturing sensitive to said radiation.

2. The method of claim 1, comprising providing said linear motor with a closed loop stator.

3. The method of claim 2, comprising providing on said linear motor at least two of said movers both simultaneously carrying one of said selected device and controlling operation of said at least two movers individually.

4. The method of claim 3, comprising more than one of said testing stations along said linear motor.

5. The method of claim 3, comprising monitoring position of each of said movers along said stator of said linear motor.

6. The method of claim 1, comprising spinning said liquid on said mover about a central axis of said container during said sensing.

7. The method of claim 6, comprising picturing with a picturing device of said testing station having a picturing axis obliquely intersecting said central axis and a plane containing a bottom surface of said container.

8. The method of claim 1, said testing station performing multiple subsequent picturing in the visible spectrum of light, the result of said picturing being exploited as an indication of solid particles present in said liquid.

9. The method of claim 1, comprising selecting all devices of said in line conveyed devices.

10. The method of claim 1, wherein the mover moves linearly on a stator of the linear motor.

11. The method of claim 1, comprising providing on a conveyor at least two of said movers both simultaneously carrying one of said selected device and controlling operation of said at least two movers individually.

12. In line device testing apparatus comprising:
   at least one testing station;
   a conveyer constructed to convey at least one selected device towards, into and from said testing station and for holding said selected device in said testing station during a testing;
   said conveyer being a linear motor with at least one mover constructed to hold said selected device;
   wherein said at least one mover being adapted to hold a container with liquid content; and
   said testing station comprising a stand still picturing arrangement for said container and said liquid contained therein and said testing station being adapted to perform said picturing of said container and liquid once or more than once subsequently.

13. The apparatus of claim 12, a stator of said linear motor being shaped in a closed loop.

14. The apparatus of claim 12, comprising two of said movers and a control unit adapted to individually control operation of said at least two movers.

15. The apparatus of claim 14, comprising more than one of said testing stations along said linear motor.

16. The apparatus of claim 14, comprising a mover-position sensor.

17. The apparatus of claim 12, said testing station comprising a radiation sensing arrangement.

18. The apparatus of claim 12, further comprising a spinning drive for said container on said mover and about a central axis of said container on said mover.

19. The apparatus of claim 12, said picturing arrangement comprising a camera, said mover being adapted to hold said container bottom down, with the bottom of said container defining a plane perpendicular to a central axis of said container, a picturing axis of said camera intersecting said central axis and said plane.

20. The apparatus of claim 19, comprising an evaluation unit, an input thereof being operationally connected to a picture output of said camera and said evaluation unit generating a signal indicative of whether said container tested in said testing station has solid particles in the liquid content.

21. The apparatus of claim 12, wherein the at least one mover is configured to move linearly on a stator of the linear motor.

* * * * *

UNITED STATES PATENT AND TRADEMARK OFFICE
CERTIFICATE OF CORRECTION

PATENT NO. : 10,435,253 B2
APPLICATION NO. : 14/905851
DATED : October 8, 2019
INVENTOR(S) : Heino Prinz It is certified that error appears in the above-identified patent and that said Letters Patent is hereby corrected as shown below:

In the Specification

Column 6, Line 29, "3 T" should read -- 3T --.

Column 6, Line 42, "2 T" should read -- 2T --.

Column 6, Line 45, "3 T" should read -- 3T --.

Column 6, Line 47, "3 T" should read -- 3T --.

Column 6, Line 48, "3 T" should read -- 3T --.

Column 6, Line 54, "2 T" should read -- 2T --.

Column 6, Line 56, "2 T" should read -- 2T --.

Column 6, Line 59, "2 T" should read -- 2T --.

Column 6, Line 61, "2 T" should read -- 2T --.

Signed and Sealed this
Twenty-fourth Day of December, 2019

Andrei Iancu
*Director of the United States Patent and Trademark Office*